United States Patent
Chao

(10) Patent No.: US 9,345,279 B2
(45) Date of Patent: May 24, 2016

(54) LINKED WAIST SUPPORT FOR WAIST BELT

(71) Applicant: HUNTEX CORPORATION, Taipei (TW)

(72) Inventor: Chia-Chang Chao, Taipei (TW)

(73) Assignee: HUNTEX CORPORATION, Taipei (TW)

( * ) Notice: Subject to any disclaimer, the term of this patent is extended or adjusted under 35 U.S.C. 154(b) by 869 days.

(21) Appl. No.: 13/671,163

(22) Filed: Nov. 7, 2012

(65) Prior Publication Data

US 2014/0123370 A1 May 8, 2014

(51) Int. Cl.
*A61F 5/00* (2006.01)
*A41F 9/00* (2006.01)
*A61F 5/03* (2006.01)
*A61F 5/02* (2006.01)

(52) U.S. Cl.
CPC . *A41F 9/00* (2013.01); *A61F 5/028* (2013.01); *A61F 5/03* (2013.01)

(58) Field of Classification Search
CPC ............. A41F 9/00; A61F 5/028; A61F 5/03; B60N 2002/445; B60N 2002/4897; B60N 2/3013; B60N 2/3065; B60N 2/309; B60N 2/366; B60N 2/4858; B60N 2/68; B60N 2/3088; B60N 2/36; B60N 2/02; B60N 2/3043; B60R 22/04; A61B 17/072; A61B 2017/003; A61B 2017/07214; A61B 17/07207; A61B 2017/306; A61B 17/0218; A61B 17/29; A61B 17/3474; A61B 2017/00278; A61B 2017/00557; A61B 2019/444; A61B 2019/4857

USPC ...................... 602/5, 19; 2/310–312
See application file for complete search history.

(56) References Cited

U.S. PATENT DOCUMENTS

| 6,322,529 | B1 | 11/2001 | Chung | |
|---|---|---|---|---|
| 6,602,214 | B2 | 8/2003 | Heinz et al. | |
| 7,727,172 | B2 * | 6/2010 | Wang | A61F 5/028 602/19 |
| 2009/0082707 | A1 * | 3/2009 | Rumsey | A61F 5/028 602/19 |
| 2010/0168630 | A1 * | 7/2010 | Cropper | A61F 5/024 602/19 |
| 2011/0213284 | A1 * | 9/2011 | Garth | A61F 5/028 602/19 |
| 2012/0253251 | A1 * | 10/2012 | Thornton | A61F 5/028 602/19 |

* cited by examiner

*Primary Examiner* — Michael Brown
(74) *Attorney, Agent, or Firm* — Muncy, Geissler, Olds & Lowe, P.C.

(57) ABSTRACT

A linked waist support for a waist belt is provided. The waist belt is formed by two strip-like woven fabrics which are connected by a fastening strap, and includes a first end link unit and a second link unit at two ends thereof. The linked waist support is disposed between and partially overlapped by the first end link unit and the second end link unit. The linked waist support comprises a base plate, a first side link unit disposed on the base plate and correspondingly linked to the first end link unit via a first linking cable, and a second side link unit disposed adjacently to the first side link unit on the base plate and correspondingly linked to the second end link unit via a second linking cable. Thus, without unfastening the waist belt, tightening force of the waist belt can be adjusted and changed with ease.

12 Claims, 5 Drawing Sheets

LINKED WAIST SUPPORT FOR WAIST BELT

FIELD OF THE INVENTION

The present invention relates to a waist support for a waist belt, and particularly to a waist support for a waist belt that adjusts tightness through pulling cables.

BACKGROUND OF THE INVENTION

Due to various reasons including the lack of exercises as well as long-term incorrect sitting and habitual hunching postures, injuries to the waist and the back are often resulted. Alternative, overeating due to over-supply of food also frequently leads to a large abdomen. Therefore, a currently market-available waist belt not only prevents a wearer having a previously injured waist or back from being again damaged by inappropriate standing or sitting postures to alleviate pains at the injured waist or back, but also keeps the wearer in a correct and upright posture at all times. Further, a waist belt may also help sculpture a wearer for a reduced waistline and enhanced body curves as a tightening force of the waist belt may prevent overeating of the wearer.

However, high tension occurs at a waist of a wearer once the waist is being bound by the waist belt, such that body stretching and activities may be made quite uneasy. Particularly when a wearer is at work, the wearer may feel that activities of the body are obstructed. Further, under the tightening force of a waist belt around a human body for a long period of time, in order to allow smooth blood circulations and for other health factors, the waist body needs to be loosened frequently for momentary stretching. So that the prior art disclosed in the U.S. Pat. No. 6,602,214, a pulley system for adjusting the tightness of a waist belt is provided. The pulley system includes a pair of pulley banks namely a first pulley bank and a second pulley bank in a juxtaposed relation. The first pulley bank can be disposed at a first distal end, and the second pulley bank can be disposed at a second distal end. The pulley system further includes a cable, which connects the first and second pulley banks and is inserted through each of the pulleys of the first and second pulley banks by turns. Through the pulleys and the cable disposed at the first and second pulley banks, the tightness of the waist belt can be adjusted. Thus, an object of conveniently adjusting and modifying the tightness of the waist belt can be achieved without unfastening the waist belt.

In the prior art disclosed in U.S. Pat. No. 6,602,214, the pulley system is short of support as only the cable is provided between the first and second pulley banks. Therefore, the U.S. Pat. No. 6,632,529 discloses with reference to FIG. 3 and FIG. 4 a waist support (201) for enhancing the support at the cable. However, several issues are incurred when implementing the waist support (201) in the U.S. Pat. No. 6,632,529. First of all, the waist support (201) is provided with a plurality of guide projections (203), which need to be engaged with guide slots (205) located in the waist belt, resulting in a complicated assembly process. Secondly, when the waist support (201) is detached, the waist support (201) may likely be lost in the event if the waist support (201) is not properly placed. Further, when pulling cords (107) are pulled, friction takes place between the guide slots (205) on the waist belt and the guide projection (203), inferring that a wearer of the waist belt needs to apply a greater amount of force for pulling the pulling cords (107).

SUMMARY OF THE INVENTION

Therefore the primary object of the present invention is to provide a linked waist support for a waist belt. Through the linked waist support, tightness of waist belt can be adjusted and changed with ease without unfastening the waist belt, so as to overcome the above issues of complicated assembly process and the likelihood of losing a back support.

To achieve the above object, a linked waist support for a waist belt is provided by the present invention. The waist belt is formed by two strip-like woven fabrics which are connected by a fastening strap, and includes a first end link unit and a second link unit at two ends thereof. The linked waist support is disposed between and partially overlapped by the first end link unit and the second end link unit. The linked waist support comprises a base plate, a first side link unit disposed on the base plate and correspondingly linked to the first end link unit via a first linking cable, and a second side link unit disposed adjacently to the first side link unit on the base plate and correspondingly linked to the second end link unit via a second linking cable.

To achieve the above object, a linked waist support of a waist belt is further provided by the present invention. The waist belt is formed by two strip-like woven fabrics which are connected by a fastening strap, and includes a first end link unit and a second link unit at two ends thereof. The linked waist support is disposed between and partially overlapped by the first end link unit and the second end link unit. The linked waist support comprises a base plate, a first side link unit disposed on the base plate and correspondingly linked to the first end link unit via a first linking cable, and a second side link unit disposed adjacently to the first side link unit on the base plate and correspondingly linked to the second end link unit via a second linking cable. The first side link unit includes at least two first unilateral interlinked two-opening threading bearing structures, or at least two bilateral interlinked three-opening threading bearing structures, and two bilateral interlinked two-opening threading bearing structures respectively disposed at two outer sides of the at least two first unilateral interlinked two-opening threading bearing structures or the at least two bilateral interlinked three-opening threading bearing structures. The second side link unit includes at least two second unilateral interlinked two-opening threading bearing structures.

In a linked waist support for a waist belt according to another embodiment of the present invention, the first side link unit further includes at least one bilateral interlinked two-opening straight threading structure disposed between the two bilateral interlinked two-opening threading bearing structures; and the second side link unit further includes a bilateral interlinked four-opening straight threading structure.

In a linked waist support of a waist belt according to another embodiment of the present invention, the at least two first unilateral interlinked two-opening threading bearing structures or the at least two bilateral interlinked three-opening threading bearing structures respectively include a first bearing and a first bearing cover for restraining axial rotational positions of the first bearing; the at least two second unilateral interlinked two-opening threading bearing structures also respectively include the first bearing and the first bearing cover; and the two bilateral interlinked two-opening threading bearing structures respectively include a second bearing and a second bearing cover for restraining the second bearing.

To achieve the above object, a linked waist support for a waist belt is further provided by the present invention. The waist belt is formed by two strip-like woven fabrics which are connected by a fastening strap, and includes a first end link unit and a second link unit at two ends thereof. The linked waist support is disposed between and partially overlapped by the first end link unit and the second end link unit. The linked waist support comprises a base plate, a first side link unit disposed on the base plate and correspondingly linked to the first end link unit via a first linking cable, and a second side link unit disposed adjacently to the first side link unit on the base plate and correspondingly linked to the second end link unit via a second linking cable. The first side link unit includes at least two first unilateral interlinked two-opening threading bearing structures, at least two bilateral interlinked three-opening threading bearing structures disposed between the at least two first unilateral interlinked two-opening threading bearing structures, and two bilateral interlinked two-opening threading bearing structures respectively disposed at two outer sides of the at least two first unilateral interlinked two-opening threading bearing structures; and the second side link unit includes at least two second unilateral interlinked two-opening threading bearing structures.

In a linked waist support for a waist belt according to another embodiment of the present invention, the first side link unit further includes at least one bilateral interlinked two-opening straight threading structure disposed between the two bilateral interlinked two-opening threading bearing structures; and the second side link unit further includes a bilateral interlinked four-opening straight threading structure.

In a linked waist support for a waist belt according to another embodiment of the present invention, the at least two first unilateral interlinked two-opening threading bearing structures, the at least two bilateral interlinked three-opening threading bearing structures, and the at least two second unilateral interlinked two-opening threading bearing structures respectively include a first bearing and a first bearing cover for restraining axial rotational positions of the first bearing; and the two bilateral interlinked two-opening threading bearing structures respectively include a second bearing and a second bearing cover for restraining the second bearing.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
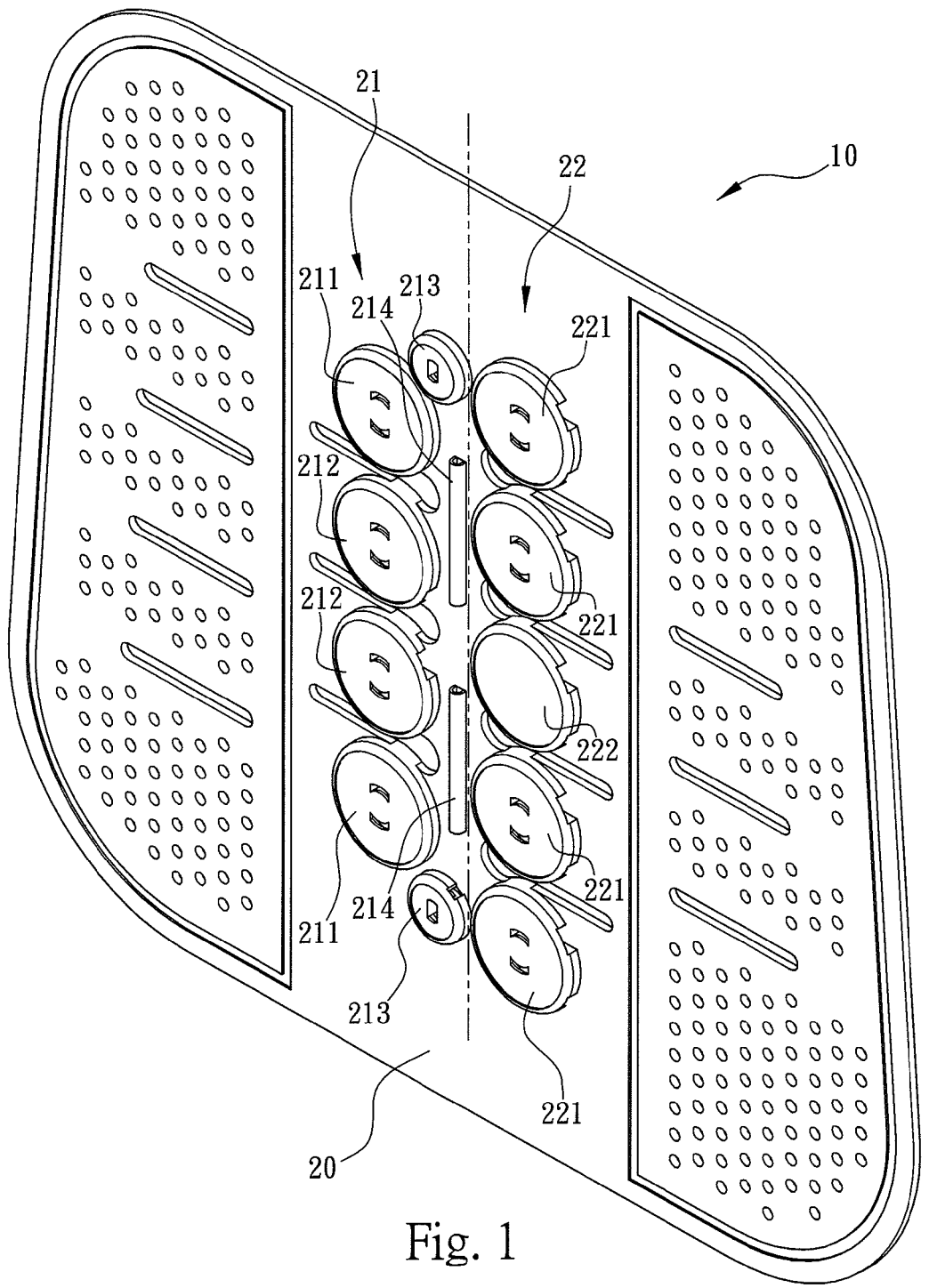
FIG. 1 is a front perspective view according to a preferred embodiment of the present invention.
Figure 2:
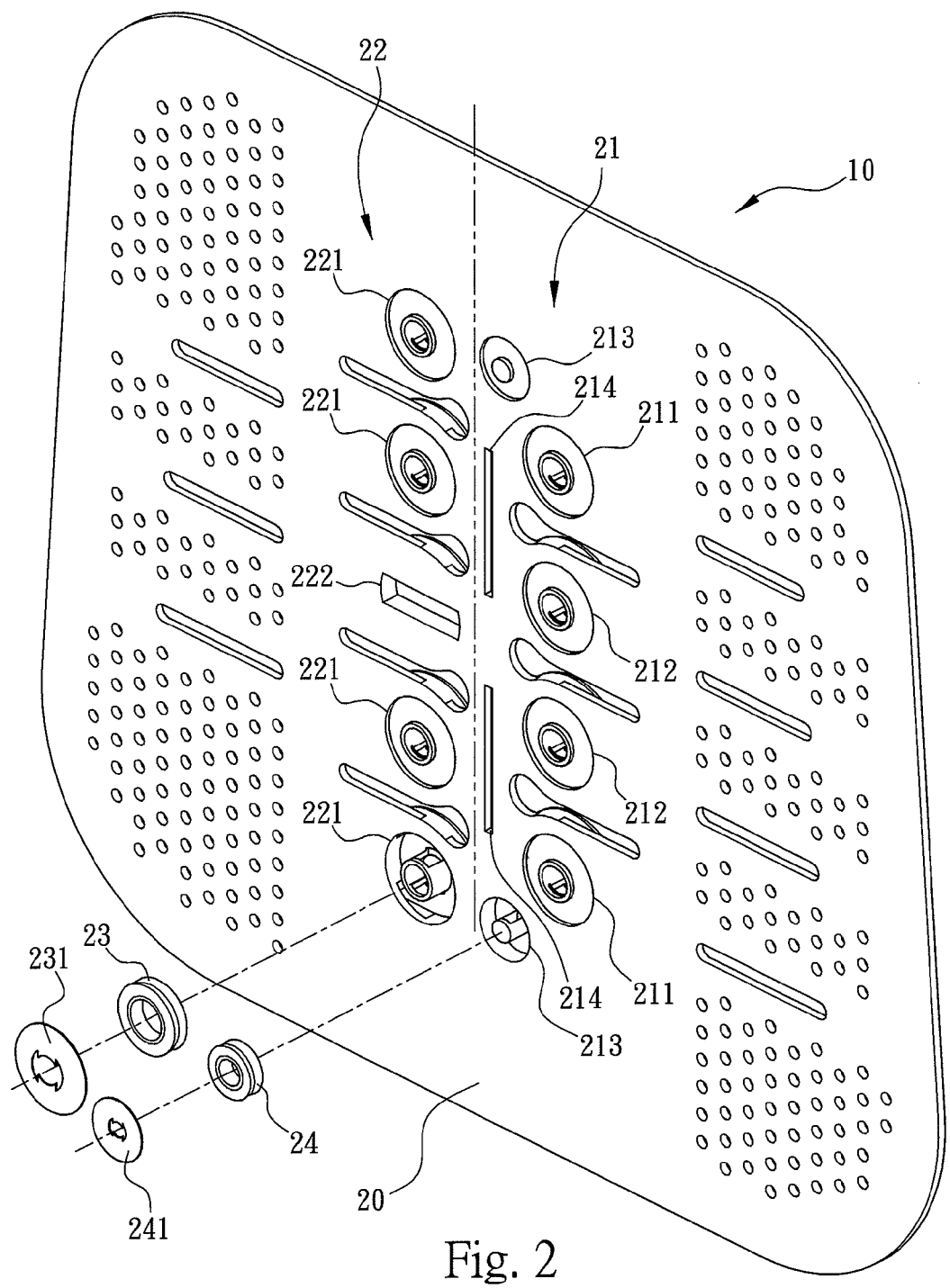
FIG. 2 is a rear perspective view of FIG. 1 according to a preferred embodiment of the present invention.
Figure 3:
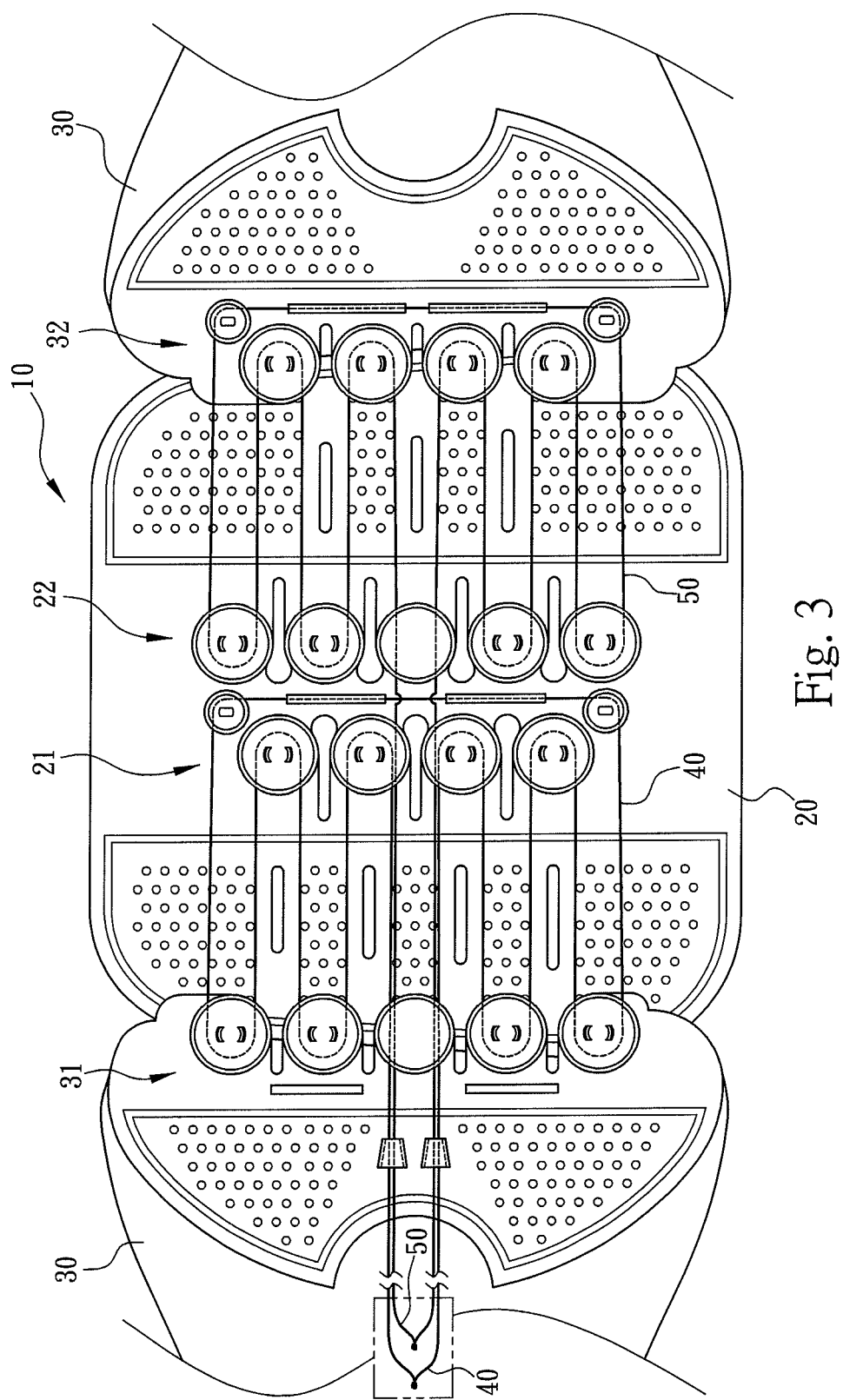
FIG. 3 is a partial schematic diagram of a linked waist support in FIG. 1 linked to a waist belt according to an embodiment of the present invention.

FIG. 1 and FIG. 2 respectively show a front perspective view and a rear perspective view of a linked waist support according to a preferred embodiment of the present invention; FIG. 3 shows a partial view of a linked waist support linked to a waist belt according to a preferred embodiment of the present invention. Referring to FIGS. 1 to 3, a waist belt 30 is formed by two strip-like woven fabrics which are connected by a fastening strap, and includes a first end link unit 31 and a second link unit 32 at two ends thereof (details of the first end link unit 31 and the second end link unit 32 may be referred to elements with denotations 22a and 22b in the U.S. Pat. No. 6,602,214). The fastening strap has a plurality of hooked materials and a plurality of corresponding looped materials. The linked waist support 10 is disposed between and partially overlapped by the first end link unit 31 and the second end link unit 32. The linked waist support 10 comprises a base plate 20 which is a flexible plate in a formed integral, a first side link unit 21 disposed on the base plate 20 and correspondingly linked to the first end link unit 31 via a first linking cable 40, and a second side link unit 22 disposed adjacently to the first side link unit 21 on the base plate 20 and correspondingly linked to second end link unit 32 via a second linking cable 50. The first side link unit 21 includes at least two first unilateral interlinked two-opening threading bearing structures 211, at least two bilateral interlinked three-opening threading bearing structures 212 disposed between the at least two first unilateral interlinked two-opening threading bearing structures 211, and two bilateral interlinked two-opening threading bearing structures 213 respectively disposed at two outer sides of the at least two first unilateral interlinked two-opening threading bearing structures 211. The second side link unit 22 includes at least two second unilateral interlinked two-opening threading bearing structures 221. The first side link unit 21 may further include at least one bilateral interlinked two-opening straight threading structure 214 disposed between the two bilateral interlinked two-opening threading bearing structures 213. The second side link unit 22 may further include a bilateral interlinked four-opening straight threading structure 222. The at least two first unilateral interlinked two-opening threading bearing structures 211, the at least two bilateral interlinked three-opening threading bearing structures 212, and the at least two second unilateral interlinked two-opening threading bearing structures 221 respectively include a first bearing 23 and a first bearing cover 231 for restraining axial rotational positions of the first bearing 23. The two bilateral interlinked two-opening threading bearing structures 213 respectively include a second bearing 24 and a second bearing cover 241 for restraining the second bearing 241. The base plate 20 may be further provided with a plurality of holes. Further, between the at least two bilateral interlinked three-opening threading bearing structures 212, between the at least two second unilateral interlinked two-opening threading bearing structures 221, and between the at least two first unilateral interlinked two-opening threading bearing structures 211 and the at least two bilateral interlinked three-opening threading bearing structures 212, holes may also be provided.

In an embodiment of the present invention, the first side unit of the linked waist support 10 may also only include at least two first unilateral interlinked two-opening threading bearing structures 211, or at least two bilateral interlinked three-opening threading bearing structures 212, and two bilateral interlinked two-opening threading bearing structures 213 respectively disposed at two outer sides of the at least two first unilateral interlinked two-opening threading bearing structures 211 or the at least two bilateral interlinked three-opening threading bearing structures 212; and the second side link unit 22 may include at least two second unilateral interlinked two-opening threading bearing structures 221. The first side link unit 21 may further include at least one bilateral interlinked two-opening straight threading structure 214 disposed between the two bilateral interlinked two-opening threading bearing structures 213; and the second side link unit 22 may further include a bilateral interlinked four-opening straight threading structure 222. The at least two first unilateral interlinked two-opening threading bearing structures 211 or the at least two bilateral interlinked three-opening threading bearing structures 212 respectively include a first bearing 23 and a first bearing cover 231 for restraining axial rotational positions of the first bearing 23; and the at least two second unilateral interlinked two-opening threading bearing structures 221 also respectively include the first bearing 23 and the first bearing cover 231. The two bilateral interlinked two-opening threading bearing structures 213 respectively include a second bearing 24 and a second bearing cover 241 for restraining the second bearing 241.

Figure 4:
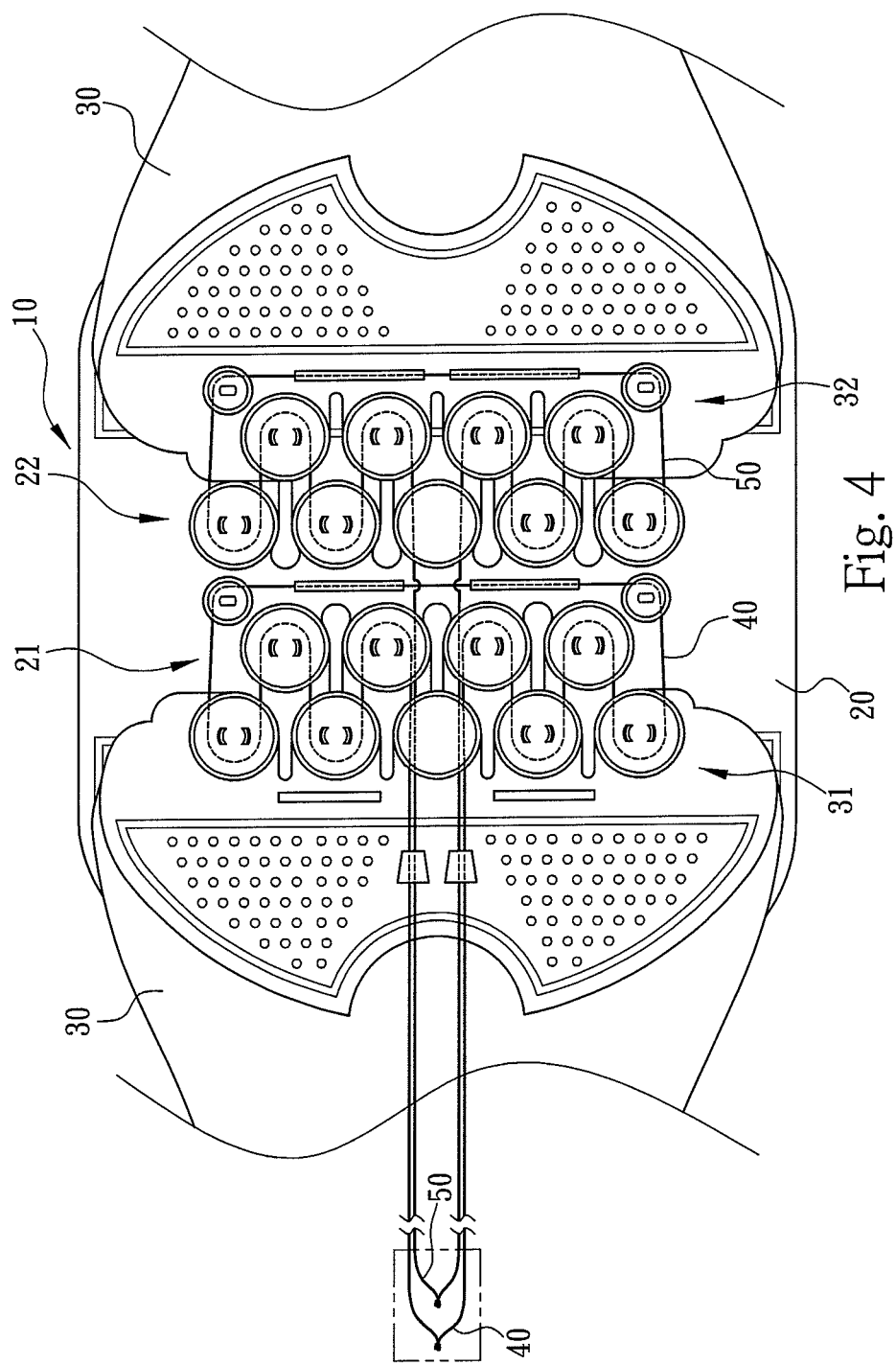
FIG. 4 is a schematic diagram illustrating successive motions of FIG. 3 according to an embodiment of the present invention.
Figure 5:
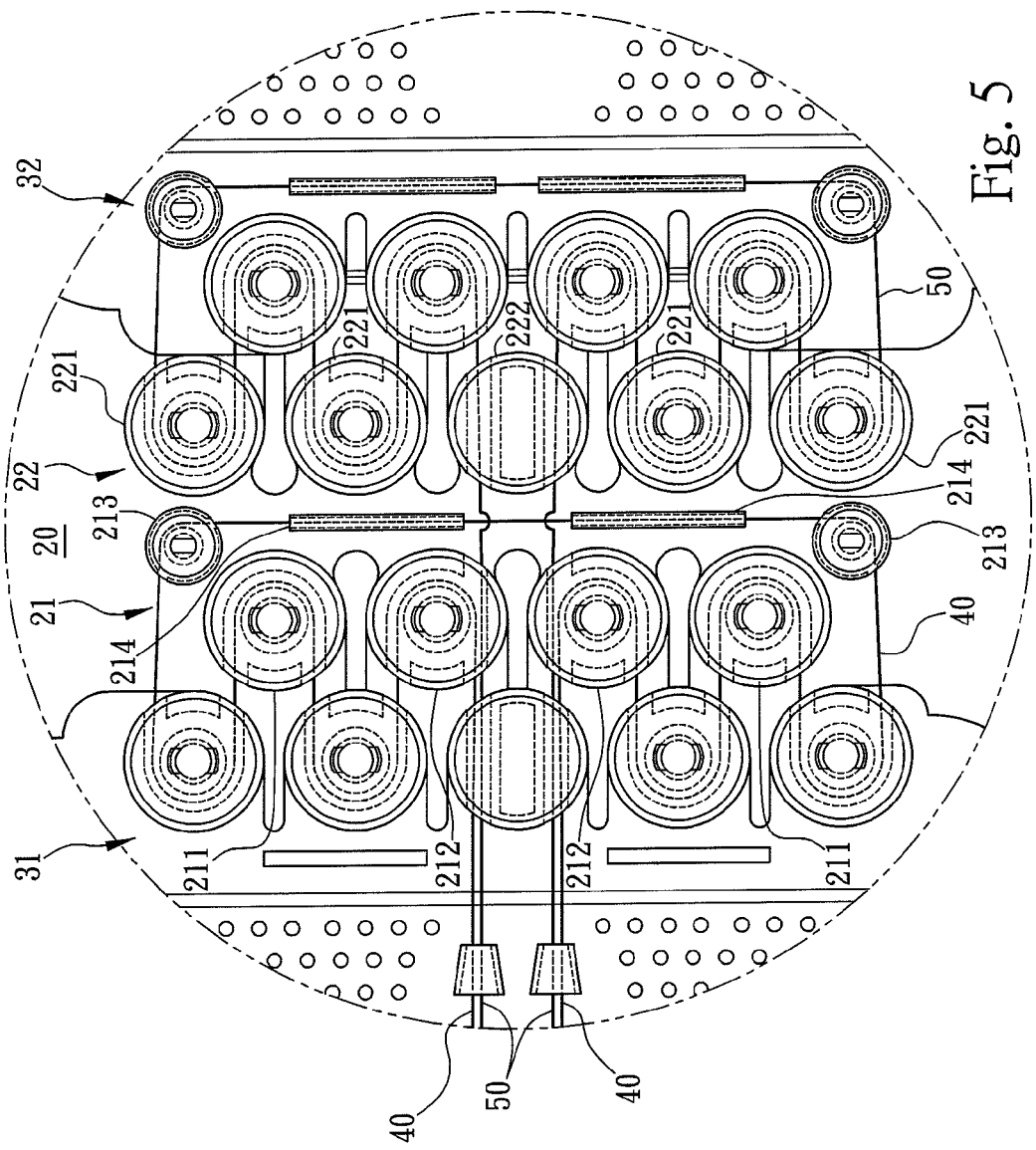
FIG. 5 is an enlarged partial view of FIG. 4 according to an embodiment of the present invention.

FIGS. 3 to 5 respectively show a schematic diagram, a schematic diagram illustrating successive motions, and a enlarged partial view of the linked waist support linked with a waist belt according to an embodiment of the present invention. It is clearly seen from the diagrams that, when a wearer is wrapped a waist belt 30 around, implementing the linked waist support 10 of the present invention, the first linking cable 40 and the second linking cable 50 can be simultaneously tightened towards a left side. Thus, the first end link unit 31 and the second end link unit 32 disposed at two ends of the waist belt 30 simultaneously approach the corresponding first side link unit 21 and the corresponding second side link unit 22 on the linked waist support 10 of the present invention, respectively.

As described in the above preferred embodiment of the present invention, the linked waist support 10 and the waist belt 30 are linked by the first linking cable 40 and the second linking cable 50 at all times, inferring that the linked waist support 10 is free from an assembly issue as well as the likelihood of getting lost. Further, in the present invention, as simultaneous tightening of the first linking cable 40 and the second linking cable 50 is implemented by axial rotations of the first side link 21 which is corresponded to the first end link unit 31 and the second side link 22 which is corresponded to the second end link unit 32, the object of adjusting and changing the tightening force of the waist belt 30 with ease can be achieved.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A linked waist support linked to a waist belt; the waist belt being formed by two strip shaped woven fabrics which are connected by a fastening strap, and including a first end link unit and a second link unit at two ends thereof; the linked waist support being disposed between and partially overlapped by the first end link unit and the second end link unit; the linked waist support comprising:
  a base plate;
  a first side link unit, disposed on the base plate, correspondingly linked to the first end link unit via a first linking cable; and
  a second side link unit, disposed adjacently to the first side link unit on the base plate, correspondingly linked to the second end link unit via a second linking cable;
  wherein the first side link unit includes at least two first unilateral interlinked two-opening threading bearing structures, and two bilateral interlinked two-opening threading bearing structures respectively disposed at two outer sides of the at least two first unilateral interlinked two-opening threading bearing structures; and the second side link unit includes at least two second unilateral interlinked two-opening threading bearing structures.

2. The linked waist support of claim 1, wherein the first side link unit further includes at least one bilateral interlinked two-opening straight threading structure disposed between the two bilateral interlinked two-opening threading bearing structures; and the second side link unit further includes a bilateral interlinked four-opening straight threading structure.

3. The linked waist support of claim 2, wherein the at least two first unilateral interlinked two-opening threading bearing structures respectively include a first bearing and a first bearing cover for restraining axial rotational positions of the first bearing; the at least two second unilateral interlinked two-opening threading bearing structures also respectively include the first bearing and the first bearing cover; and the two bilateral interlinked two-opening threading bearing structures respectively include a second bearing and a second bearing cover for restraining the second bearing.

4. The linked waist support of claim 1, wherein the at least two first unilateral interlinked two-opening threading bearing structures respectively include a first bearing and a first bearing cover for restraining axial rotational positions of the first bearing; the at least two second unilateral interlinked two-opening threading bearing structures also respectively include the first bearing and the first bearing cover; and the two bilateral interlinked two-opening threading bearing structures respectively include a second bearing and a second bearing cover for restraining the second bearing.

5. The linked waist support of claim 1, wherein the first side link unit includes at least two first unilateral interlinked two-opening threading bearing structures, at least two bilateral interlinked three-opening threading bearing structures disposed between the at least two first unilateral interlinked two-opening threading bearing structures, and two bilateral interlinked two-opening threading bearing structures respectively disposed at two outer sides of the at least two first unilateral interlinked two-opening threading bearing structures; and the second side link unit includes at least two second unilateral interlinked two-opening threading bearing structures.

6. The linked waist support of claim 5, wherein the first side link unit further includes at least one bilateral interlinked two-opening straight threading structure disposed between the two bilateral interlinked two-opening threading bearing structures; and the second side link unit further includes a bilateral interlinked four-opening straight threading structure.

7. The linked waist support of claim 6, wherein the at least two first unilateral interlinked two-opening threading bearing structures, the at least two bilateral interlinked three-opening threading bearing structures, and the at least two second unilateral interlinked two-opening threading bearing structures respectively include a first bearing and a first bearing cover for restraining axial rotational positions of the first bearing; and the two bilateral interlinked two-opening threading bearing structures respectively include a second bearing and a second bearing cover for restraining the second bearing.

8. The linked waist support of claim 5, wherein the at least two first unilateral interlinked two-opening threading bearing structures, the at least two bilateral interlinked three-opening threading bearing structures, and the at least two second unilateral interlinked two-opening threading bearing structures respectively include a first bearing and a first bearing cover for restraining axial rotational positions of the first bearing; and the two bilateral interlinked two-opening threading bearing structures respectively include a second bearing and a second bearing cover for restraining the second bearing.

9. A linked waist support linked to a waist belt; the waist belt being formed by two strip shaped woven fabrics which are connected by a fastening strap, and including a first end link unit and a second link unit at two ends thereof; the linked waist support being disposed between and partially overlapped by the first end link unit and the second end link unit; the linked waist support comprising:

a base plate;

a first side link unit, disposed on the base plate, correspondingly linked to the first end link unit via a first linking cable; and a second side link unit, disposed adjacently to the first side link unit on the base plate, correspondingly linked to the second end link unit via a second linking cable, wherein the first side link unit includes at least two bilateral interlinked three-opening threading bearing structures, and two bilateral interlinked two-opening threading bearing structures respectively disposed at two outer sides of the at least two bilateral interlinked three-opening threading bearing structures; and the second side link unit includes at least two second unilateral interlinked two-opening threading bearing structures.

10. The linked waist support of claim 9, wherein the first side link unit further includes at least one bilateral interlinked two-opening straight threading structure disposed between the two bilateral interlinked two-opening threading bearing structures; and the second side link unit further includes a bilateral interlinked four-opening straight threading structure.

11. The linked waist support of claim 10, wherein the at least two bilateral interlinked three-opening threading bearing structures respectively include a first bearing and a first bearing cover for restraining axial rotational positions of the first bearing; the at least two second unilateral interlinked two-opening threading bearing structures also respectively include the first bearing and the first bearing cover; and the two bilateral interlinked two-opening threading bearing structures respectively include a second bearing and a second bearing cover for restraining the second bearing.

12. The linked waist support of claim 9, wherein the at least two bilateral interlinked three-opening threading bearing structures respectively include a first bearing and a first bearing cover for restraining axial rotational positions of the first bearing; the at least two second unilateral interlinked two-opening threading bearing structures also respectively include the first bearing and the first bearing cover; and the two bilateral interlinked two-opening threading bearing structures respectively include a second bearing and a second bearing cover for restraining the second bearing.

* * * * *